United States Patent [19]
Eva

[11] Patent Number: 6,103,904
[45] Date of Patent: Aug. 15, 2000

[54] SKRAUP REACTION PROCESS FOR SYNTHESIZING QUINOLONES

[75] Inventor: Ronald R. Eva, Bahama, N.C.

[73] Assignee: BASF Corporation, Mount Olive, N.J.

[21] Appl. No.: 08/896,556

[22] Filed: Jul. 17, 1997

[51] Int. Cl.[7] ...................... C07D 215/16; C07D 215/20; C07D 215/36; C07D 215/60
[52] U.S. Cl. .......................... 546/152; 546/153; 546/159; 546/168; 546/171; 546/178; 546/181; 546/182
[58] Field of Search ...................................... 546/152, 153, 546/159, 168, 171, 178, 181, 182

[56] References Cited

U.S. PATENT DOCUMENTS

| | | | |
|---|---|---|---|
| 4,157,445 | 6/1979 | Fitton | 546/181 |
| 4,617,395 | 10/1986 | Dockner | 546/178 |
| 5,382,502 | 1/1995 | Lau | 430/552 |

FOREIGN PATENT DOCUMENTS 3719014  3/1989  European Pat. Off. .

OTHER PUBLICATIONS

CA 98:16557, abstract of Roy, Indian J Technol, 1982, vol. 20(8), pp 330–332.
CA 120:163934, abstract of Song, J Heterocyclic Chem, 1993, vol. 30(1), pp 17–21.

*Primary Examiner*—D. Margaret M. Mach
*Attorney, Agent, or Firm*—Joanne P. Will

[57] ABSTRACT

The present invention relates to an improved Skraup reaction process wherein pressure is applied during the reaction and the number of equivalents of sulfuric acid utilized is reduced.

1 Claim, No Drawings

SKRAUP REACTION PROCESS FOR SYNTHESIZING QUINOLONES

FIELD OF THE INVENTION

The present invention relates to an improved Skraup reaction process for synthesizing quinolones.

BACKGROUND

The Skraup reaction is the general method, well known to those skilled in the art of organic chemistry, for synthesizing quinolones, in which aniline or a substituted aniline is treated with glycerol, sulfuric acid, and an oxidizing agent such as $As_2O_5$, ferric salts, or the nitro compound corresponding to the amine used.

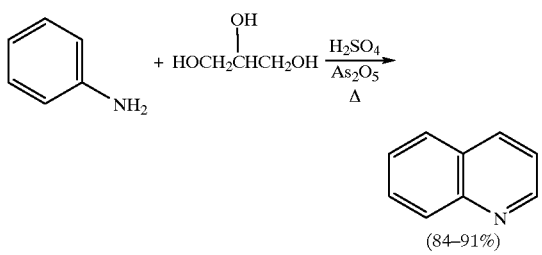

(84–91%)

The mechanism of the Skraup reaction involves initial dehydration of the glycerol to give acrolein, which undergoes a 1,4-addition by the aniline. The resulting β-anilinopropionaldehyde is then cyclized to a dihydroquinoline, which is finally oxidized to give the product.

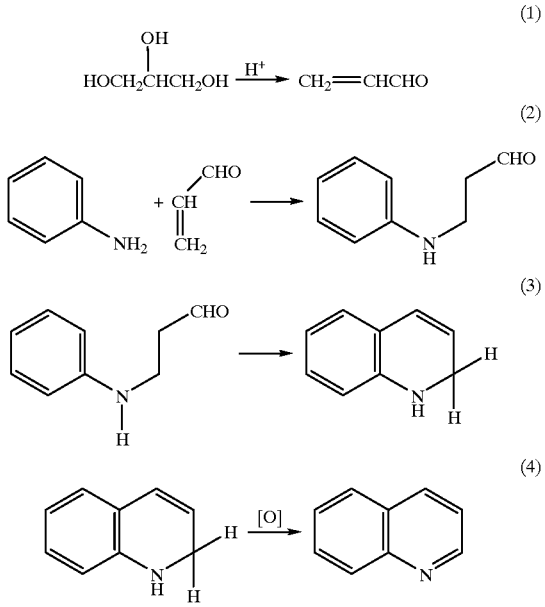

Identical results are obtained if an α,β-unsaturated ketone or aldehyde is substituted for the glycerol.

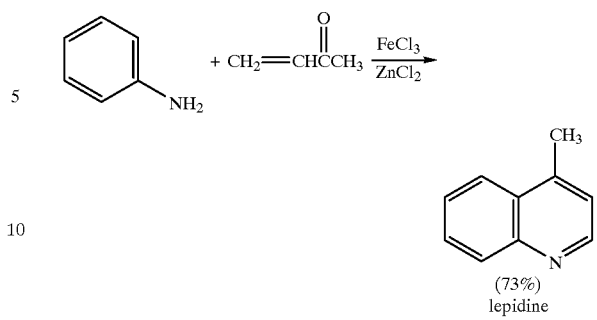

(73%)
lepidine

If a saturated aldehyde is used, an initial aldol condensation occurs to give an α,β-unsaturated aldehyde normal condensation (Döbner-Miler reaction).

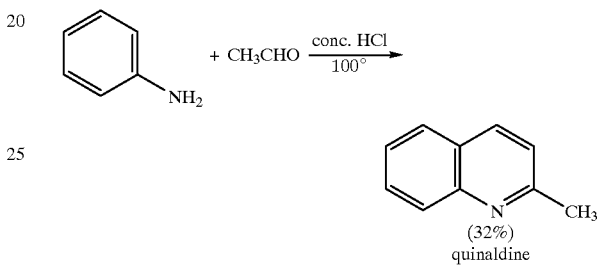

(32%)
quinaldine

In some of these cases an oxidizing agent is not included; in these cases unsaturated reaction intermediates probably serve as oxidizing agents, but this point has not been established. The Skraup synthesis is extremely versatile; almost any desired quinoline may be prepared by using the proper combination of aniline and aldehyde, so long as the reagents will survive the hot acid conditions. A more complex example is

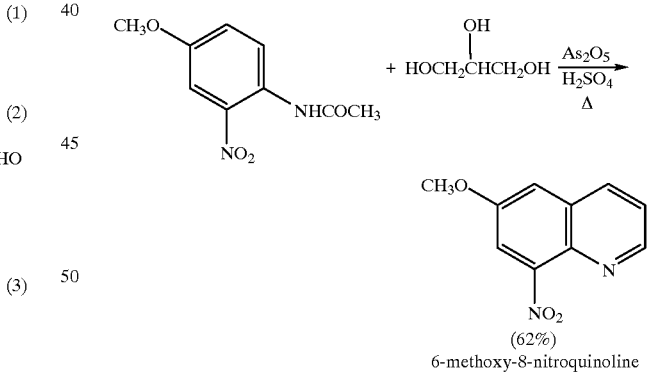

(62%)
6-methoxy-8-nitroquinoline

See, Streitweiser & Heathcock, *Introduction to Organic Chemistry*, Chapter 35, 1976 and *The Chemistry of Heterocyclic Compounds, A Series of Monographs*, Edit. A. Weissberger and Edw. C. Taylor, Quinolones—Part I (hereinafter "Quinolones—Part I").

However, Skraup reactions generally have 50% yields and are typically very "dirty" reactions. Thus, the art has attempted to improve the yield of Skraup reactions. Specifically, U.S. Pat. No. 4,157,445 assigned to Union Carbide, discloses an improved method for the synthesis or quinoline and substituted quinolines which comprises interacting: a mixture of a nitro-substituted aromatic hydrocarbon containing 6 to 18 aromatic ring carbon atoms and a replaceable hydrogen atom ortho to each nitro group with ethylenically unsaturated hydrocarbons in the presence of a metal coordination complex catalyst. The efficiency is disclosed as being 54% and 50% for 2-methyl-quinolone; 88% for 2,6 dimethyl-quinolone; 1.9% for quinolone.

U.S. Pat. No. 4,617,395, assigned to BASF AG, discloses a process for preparing quinolones wherein unsubstituted or substituted aniline is reacted with acrolein or another αβ-unsaturated aldehyde at elevated temperatures, in a high-boiling mineral oil. Yields ranged from 45% to 76%.

U.S. Pat. No. 5,382,502, assigned to Eastman Kodak, discloses the preparation of hydroxy quinolone compounds having yields of 61%, 65%, 57%, 67% and 45%.

U.S.S.R. disclosure SU 1,416,487, Dzhemilev, U. M.; Selimov, F. A.; Akhmetov, A. Zh. (Bashkir Institute of Chemistry) Aug. 15, 1988, Appl. 4,126,063, Jul. 28, 1986, from Otkrytiya, Izabret. 1988, (30), discloses a method of producing alkyl derivatives of quinolone. Specifically, 2,3-dialkylquinolines are prepared by the reaction of nitrogen-containing benzene derivatives with oxygen-containing aliphatic compounds in the presence of a mixture of Fe acetylacetonate, $PPh_3$, and trialkylaluminum, at a molar ratio of 0.9–1.5:2–6:2–5, as the catalyst. The reaction is carried out at 180–220° for six hours in an argon atmosphere in an autoclave.

Finally, DE 3,719,014, assigned to BASF AG, discloses an improved yield Skraup process for the preparation of the formula:

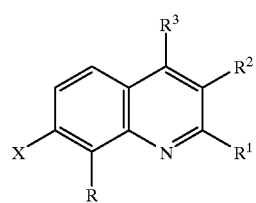

(I)

where the following signify

R $C_1$–$C_5$-Alkyl, $R^1$, $R^2$, $R^3$ Hydrogen or $C_1$–$C_5$-Alkyl, and

X Hydrogen or halogen with the stipulation that R also represents hydrogen, when X represents hydrogen, through reaction of the anilines with the formula:

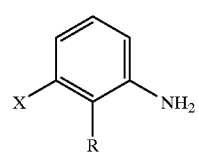

(II)

with α, β-unsaturated aldehydes or ketones with the formula:

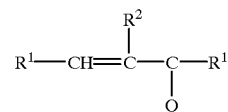

(III)

in sulfuric acid (70 wt. % to 85 wt. %) in the presence of catalytic amounts of iodine at increased temperature.

The reaction is carried out as follows: Aldehyde or ketone (III) is added to a solution of aniline (II) preheated to 100 up to 140° C. in sulfuric acid and catalytic amounts of iodine during a 60 to 90 minute period, during which the temperature of the reaction mixture is not allowed to drop below 100° C., if possible. The temperature should be maintained within the range of approximately 100 to 150° C., preferably in the range of 115 to 30° C. At the end of the reflux, the reaction solution is neutralized at 70 to 100° C. through the addition of an aqueous lye, for example, soda lye, and the desired product precipitates from the aqueous phase as an organic phase.

A molar ration of 1:1 to 1:1.5 is appropriate for the parent material, and preferably a ration of 1:1.1 to 1:1.3 aniline (II) to aldehyde or ketone (III). The molar quantity of sulfuric acid is 2 to 8 mole, preferably 2.5 to 6 mol per mole of aniline II, most preferably 6 moles of sulfuric acid.

The catalytic quantities of iodine required for the reaction can be added to the reaction mixture in the form of inorganic iodine compounds, for example, as elementary iodine, as hydroiodic acid or as metal iodide, such as calcium iodide or sodium iodide, in solid or liquid form, for example, in an aqueous solution.

The yields for the reaction described in DE 3,719,014 are 92.8%, 86.8%, 75%, 75.7%, and 90.7%.

On the other hand, Applicant's improved process reduces the equivalents of acid necessary to carry out the reaction sequence by applying pressure during the reaction sequence.

SUMMARY

A process for improving the quinoline yield of a Skraup reaction comprising the steps of:
a) reacting 2.75–5.0 molar equivalents of 75 to 80% sulfuric acid with a substituted or unsubstituted aniline at a temperature of 100 to 130° C.;
b) adding catalyst at a temperature of 130–135° C.;
c) adding substituted or unsubstituted unsaturated aldehyde or glycerol at a temperature of 135–140° C. while refluxing;
d) allowing the pressure to increase to 2–7 psig;
e) allowing the temperature to increase to 150–153° C.

DETAILED DESCRIPTION

A process for improving the quinoline yield of a Skraup reaction comprising the steps of:
a) reacting 2.75–5.0 molar equivalents of 75 to 80% sulfuric acid with a substituted or unsubstituted aniline at a temperature of 100 to 130° C.;
b) adding catalyst at a temperature of 130–135° C.;
c) adding substituted or unsubstituted unsaturated aldehyde or glycerol at a temperature of 135–140° C. while refluxing;
d) allowing the pressure to increase to 2–7 psig;
e) allowing the temperature to increase to 150–153° C.

The Skraup reaction described in DE 3,719,014 provides a basic description of how the Skraup reaction is run under laboratory conditions and is incorporated by reference herein.

In the present invention, which is particularly useful on a commercial scale, 2.75–5.0 equivalents of sulfuric acid are added to process water in a clean 1000 gallon glass-lined reactor; preferably 3–4.5 equivalents; most preferably, 3–4 equivalents. To the resulting 80% aqueous sulfuric acid solution is added a substituted or unsubstituted aniline compound, capable of forming the quinoline structure under the reaction conditions. Representative substituted or unsubstituted aniline compounds are described in "Quinolones–Part I," page 247–259, Table 1, incorporated by reference herein. During said aniline compound charge, the temperature is allowed to exotherm from approximately 100° C. to 140° C., and is maintained in a temperature range of 100°–140° C. throughout the addition of the remaining aniline compound. Appropriate catalysts, including but not limited to, iodide and iodide salts such as sodium and potassium iodide, mild oxidizing agents, such as nitroaromatics and arsenic compounds, is added to the warm solution and the batch temperature is maintained at 110°–140°. Other appropriate catalysts are described in DE 3,719,014, incorporated by reference herein. Unsaturated substituted and unsubstituted aldehydes or glycerols, such as but not limited to, acrolein, crotonaldehyde, methacrolein, methyl vinyl ketone or ethyl vinyl ketone, described in DE 3,719,014, incorporated by reference herein, are added to the reactor over a period of 30 minutes to 2 hours and the temperature is maintained at 135–140° C. with the condenser set for total reflux. Upon completion of said aldehyde or glycerol addition, the reactor pressure is allowed to increase from 2 to 7 psig, preferably 3–6 psig, most preferably 4–6 psig; and the aqueous distillate is removed over 5–6 hours until the batch temperature increases to 145°–160° C. The batch is then sampled and analyzed by gas chromatography (GC) to assure that the aniline compound level is less than 0.2%.

When the aniline compound level is less than 0.2% the batch is quickly cooled, and isolation of the product is completed in a manner, required for the individual material, according to those skilled in the art.

What is claimed is:

1. A process for improving the quinoline yield of a Skraup reaction comprising the steps of:

a) reacting 2.75–5.0 molar equivalents of 75–80% sulfuric acid with a substituted or unsubstituted aniline at a temperature of 100 to 130° C.;

b) adding catalyst at a temperature of 130–135° C.;

c) adding substituted or unsubstituted unsaturated aldehyde or glycerol at a temperature of 135–140° C. while refluxing;

d) allowing the pressure to increase to 2–7 psig;

e) allowing the temperature to increase to 150–153° C.

\* \* \* \* \*